United States Patent

Malowaniec

[11] Patent Number: 6,049,915
[45] Date of Patent: Apr. 18, 2000

[54] ITEM OF CLOTHING, ESPECIALLY DISPOSABLE CLOTHING FOR USE ONCE ONLY

[75] Inventor: Krzysztof D. Malowaniec, Heidenheim, Germany

[73] Assignee: Paul Hartmann AG, Heidenheim, Germany

[21] Appl. No.: 08/913,295

[22] PCT Filed: Mar. 1, 1996

[86] PCT No.: PCT/EP96/00865

§ 371 Date: Sep. 11, 1997

§ 102(e) Date: Sep. 11, 1997

[87] PCT Pub. No.: WO96/29036

PCT Pub. Date: Sep. 26, 1996

[30] Foreign Application Priority Data

Mar. 18, 1995 [DE] Germany ............... 195 09 953

[51] Int. Cl.[7] ................................. A41B 9/00
[52] U.S. Cl. .................... 2/400; 2/87; 604/366; 128/287
[58] Field of Search ................. 2/400, 114, 51, 2/87; 604/366; 128/287

[56] References Cited

U.S. PATENT DOCUMENTS

| | | | |
|---|---|---|---|
| H1575 | 8/1996 | Daugherty et al. | 604/366 |
| 3,886,941 | 6/1975 | Duane et al. | 128/287 |
| 4,731,066 | 3/1988 | Korpman | 604/366 |
| 5,643,240 | 7/1997 | Jackson et al. | 604/366 |
| 5,667,864 | 9/1997 | Landoll | 604/366 |

*Primary Examiner*—John J. Calvert
*Assistant Examiner*—Robert H. Muromoto, Jr.
*Attorney, Agent, or Firm*—Jones, Tullar & Cooper, P.C.

[57] ABSTRACT

The invention relates to an item of clothing, especially disposable clothing for use once only, with at least one essentially inelastic layer (12) of a soft, flexible and plastic material and a layer (11) of elastic material which extends over at least a partial region of the inelastic layer (12) and is secured thereto to form an elastic component (10). In order to be able to make the elastic component in such an item of clothing easily, there is a plurality of incisions (14) in the inelastic layer (12) in the region of the elastic layer (11) which do not penetrate the elastic layer. The elastic layer may thus also contain absorbent materials.

10 Claims, 2 Drawing Sheets

FIG. 1
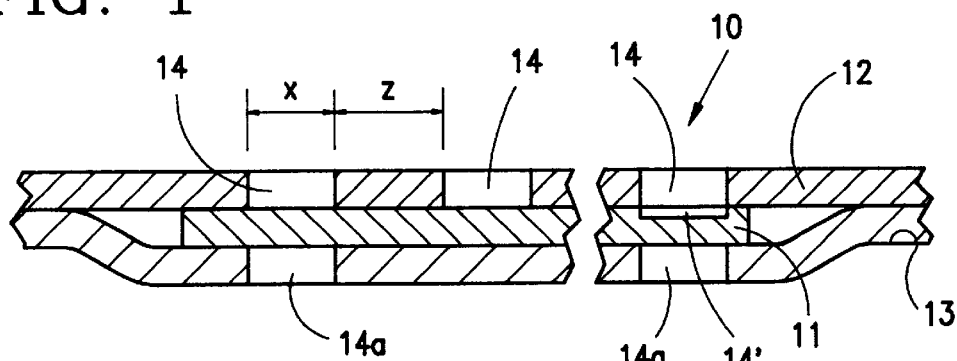
FIG. 2
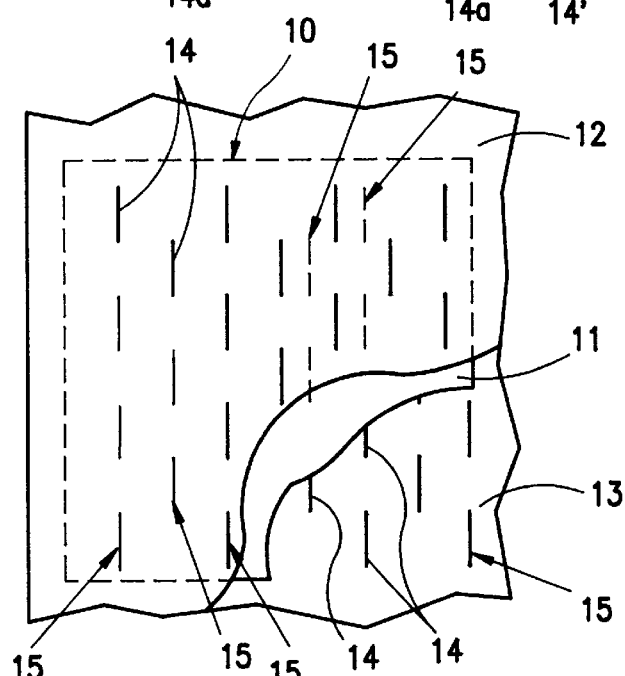
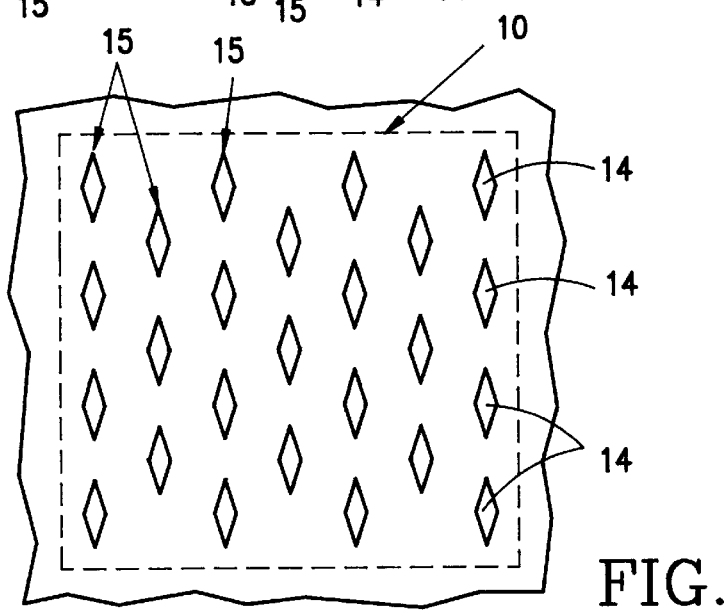
FIG. 3

ITEM OF CLOTHING, ESPECIALLY DISPOSABLE CLOTHING FOR USE ONCE ONLY

BACKGROUND OF THE INVENTION

1. Technical Field

The present invention concerns an article of clothing, especially disposable clothing for one-time use, comprising at least one primary inelastic layer or a soft, flexible, and plastic material, a layer of an elastic material, which covers at least a partial segment of at least one of the inelastic segments, and is connected to the inelastic layer for the purpose of forming an elastic element, in which a plurality of incisions, preferably arranged in rows, are made into the inelastic layer where it overlaps with the elastic layer.

2. Prior Art

In order to ensure a secure and comfortable fit, with articles of clothing, particularly disposable or single-use diapers for children or incontinent individuals, the articles of clothing must include elastic segments, at least in the vicinity of a band that is placed around the hips and stomach. This also applies to the elastic sections in the legs and arms of single-use clothing.

Disposable diapers known in the art published international patent applications (WO 94/05241, WO 93/25171; WO 92/22274; WO 92/22273) include an elastic element or elastic zone, located in the part of the band located near adhesive strips used for closure, which contains a layer made of elastic material. This layer is sandwiched between a liquid-proof foil and a fleece layer, and is connected to these two materials.

To ensure that the inelastic but plastic foil and the fleece, which is also inelastic but plastic, can conform to the elastic zone of the elastic layer without substantially affecting the expansion of the elastic layer, the foil, the elastic layer, and the fleece are mechanically stressed together, so that the two inelastic but plastic layers are forcefully over-stretched and consequently lengthened in the vicinity of the elastic layer, as well as being connected to the elastic layer.

This is intended to create an elastic zone in which the over-stretched inelastic materials are virtually no longer capable of preventing elastic expansion of the elastic material. However, this makes it difficult to stretch the inelastic layers, i.e., the foil and the fleece, in such a targeted manner that they are capable of allowing for the correct degree of expansion when subsequent expansion of the elastic zone is desired. Another difficulty consists in maintaining the elasticity of the elastic layer in spite of its overexpansion or in adjusting the desired degree of expandability.

In a diaper known in the art under U.S. Pat. No. 4,371,066, external slits are included in the waist area on both sides of the diaper to increase diaper elasticity in that area. Openings form when the material is expanded.

SUMMARY OF THE INVENTION

Based on the above, an object of the present invention is to provide a laminate that is tear-proof in spite of the incisions, and in which the incisions in the vicinity of elastic element do not continue throughout all three layers, thus ensuring impermeability to liquid in this region.

According to the present invention, this object is achieved in a generic article of clothing in that the incisions in the first inelastic layer are laterally displaced against the incisions in the second inelastic layer.

The inclusion of the incisions in the inelastic layer, as specified in the present, ensures that the incisions do not continue undesirably through all three layers or that they can damage the inelastic layer in such a way that it tears in response to unwanted expansion. This, in turn, ensures that the article of clothing also provides the requisite level of impermeability to liquid in the region of the elastic element.

Thus, the incisions in the inelastic layers can be expanded to form rhombic openings, thus allowing the corresponding layers to move as desired in response to expansion in the elastic layer. If necessary, the elasticity of the elastic element can be adjusted through appropriate selection of incision length, spacing between incisions within a row, and spacing between the rows.

BRIEF DESCRIPTION OF THE DRAWINGS

Four figures will be used to describe the present invention in greater detail. The figures depict the following:

FIG. 1: A schematic cross-section through an elastic element of an article of clothing, as described in the present invention.

FIG. 2: An aerial view of a segment of an article of clothing, as described in the present invention, in the vicinity of an elastic element.

FIG. 3: An aerial view, corresponding to that depicted in FIG. 2, of an elastic element in an expanded state.

DETAILED DESCRIPTION OF THE PRESENT INVENTION

Figure 4:
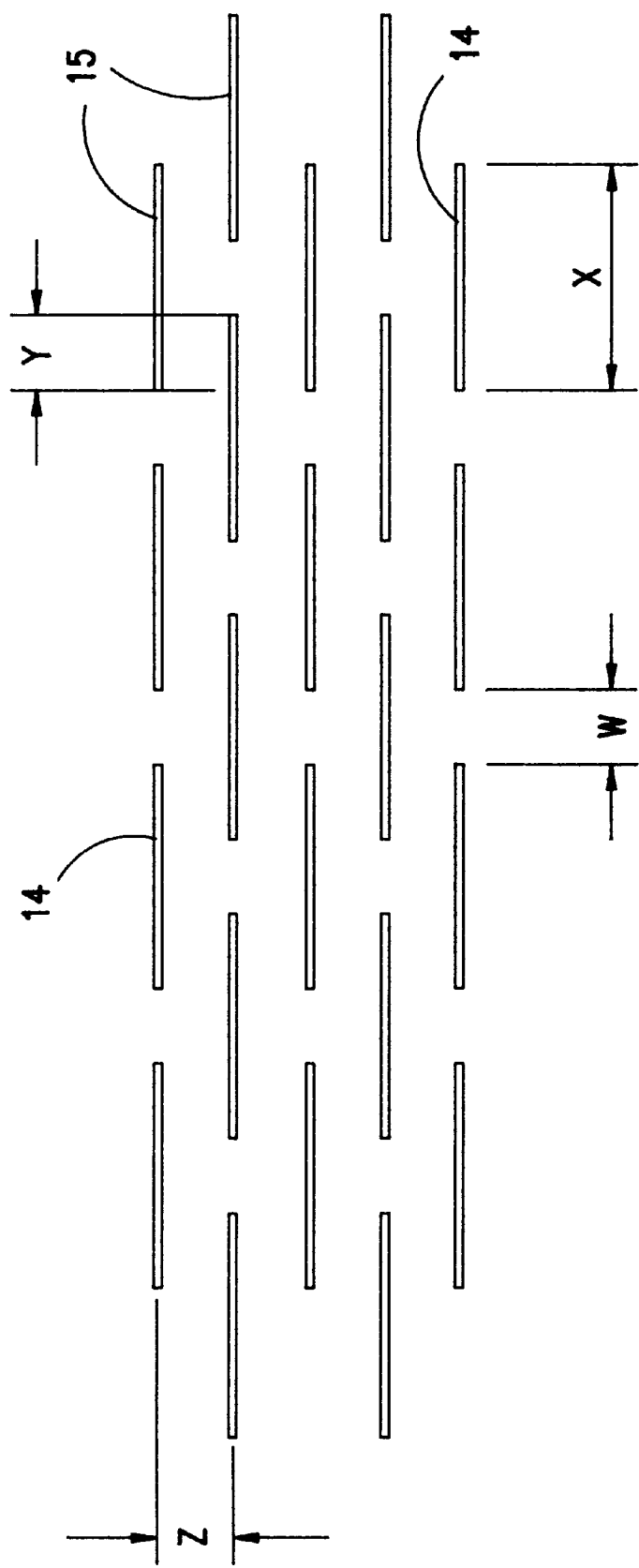
FIG. 4: A schematic depiction of the incision area.

As depicted in FIG. 1, the article of clothing described in the present invention includes a layer 11 of elastic material in the vicinity of an elastic element 10, which is sandwiched between two inelastic layers 12 and 13 and is connected to these layers.

One of the inelastic layers 12 may, for example, be composed of a soft, flexible, plastic foil that is impermeable to liquid, such as the material used to form the exterior portion of disposable diapers, i.e., the surface facing away from the body. The other inelastic layer 13 may, for example, be composed of a soft, flexible, and plastic fleece, such as that normally used to form the inner surface of disposable diapers. If at least one of the two inelastic layers 12 and 13 is composed of a material impermeable to liquid, a material impermeable to liquid is also used for the elastic layer.

Preferably, incisions 14, which are cut into the plastic foil 12 and the plastic fleece 13 in the vicinity of elastic layer 11, only extend through the plastic foil 12 and the plastic fleece 13 (see FIG. 2) and, as depicted on the left-hand side of FIG. 1, do not continue into the elastic layer 11.

As depicted on the right-hand side of FIG. 1, the incisions 14 may also extend into the elastic layer 11, with the incision 14 in the elastic layer 11 only penetrating slightly into rather than extending throughout the elastic layer 11.

The incisions may be arranged in congruent fashion in both the inelastic plastic layer 12 and in plastic layer 14 (at 14a).

As depicted in FIG. 2, the incisions 14 are arranged in rows 15, with the incisions 14 in adjacent rows laterally displaced against one another in the longitudinal direction of the rows. Furthermore, the rows 15 of incisions 14 in the plastic foil 12 are laterally displaced against the rows 15 of incisions 14 in the plastic fleece 13. This ensures that if there are incisions 14 in the elastic layer 11, they will be positioned in such a way so as to prevent excessive damage to the elastic layer and ensure that it remains operational.

As depicted in FIG. 3, the incisions 14 expand to form rhombic openings when the elastic element 10 expands in the direction of the double arrow (D).

If this type of element is used in a diaper or similar article, the incisions 14 do not adversely affect the triple-layer diaper material's impermeability to liquid in the vicinity of the elastic element 10, even when the elastic element 10 is in an expanded state, as the rhombic openings that form in this area as a result of the incisions 14 are covered by the elastic layer, thus preventing liquid from escaping through the openings.

In an advantageous modification, the elastic layer may also either be composed of or contain a porous material, with the porous material of fibers and/or hydrogels with substantial liquid absorption properties.

Optimal dimensions are as follows: At an incision 14 length x (see FIG. 4) and a distance w between the incisions, as well as a distance z between the incision rows 15 and an overlapping region y between the incisions in two adjacent rows, the value z should roughly correspond to the values y and/or w, with the value z ranging between 1 and 4 mm. The length x should be equal to about 3z. Elasticity improves as the values y and x increase.

I claim:

1. An article of clothing, comprising:

first and second primarily inelastic layers of a soft, flexible and plastic material;

a layer of an elastic material sandwiched between said first and second inelastic layers, covering at least a partial segment of said first and second inelastic layers; and a plurality of incisions included in said first and second inelastic layers where they overlap with said layer of elastic material, wherein the incisions in said first inelastic layer being laterally displaced with respect to the incisions in the second inelastic layer, and wherein said layer of an elastic layer is connected to one of said first and second inelastic layers for forming an elastic element.

2. The article as defined in claim 1, wherein the incisions only partially penetrate into said one of said first and second inelastic layers.

3. The article as defined in claim 1, wherein the incisions completely penetrate said one of said first and second inelastic layers.

4. The article as defined in claim 1, wherein one of said first and second inelastic layers contains porous material.

5. The article as defined in claim 1, wherein the incisions in said one of said first and second inelastic layers form rows, and wherein the distance between adjacent rows of incisions is equal approximately to the length by which the incisions in one of said adjacent rows overlaps with the incisions in the other of said adjacent rows.

6. The article as defined in claim 1, wherein the incisions in said one of said first and second inelastic layers form rows, and wherein the distance between adjacent rows of incisions is equal approximately to the distance between incisions in one of said adjacent rows.

7. The article as defined in claim 1, wherein the incisions in said one of said first and second inelastic layers form rows, and wherein the length of an incision is between two to four times the length of the distance between adjacent rows of incisions.

8. The article as defined in claim 1, wherein the incisions in said one of said first and second inelastic layers form rows, and wherein the length of an incision is three times the length of the distance between adjacent rows of incisions.

9. The article as defined in claim 1, wherein the incisions are approximately 1–4 mm in length.

10. The article as defined in claim 1, wherein the article comprises a disposable article of clothing for one-time use.

* * * * *